United States Patent [19]

Karras et al.

[11] Patent Number: 4,464,054

[45] Date of Patent: Aug. 7, 1984

[54] COLORIMETER INSTRUMENT WITH FIBER OPTIC RING ILLUMINATOR

[75] Inventors: Philip Karras, Silver Spring; Jack A. Ladson, Olney, both of Md.

[73] Assignee: Pacific Scientific Company, Anaheim, Calif.

[21] Appl. No.: 382,618

[22] Filed: May 27, 1982

[51] Int. Cl.$^3$ .................................................. G01J 3/50
[52] U.S. Cl. ...................... 356/406; 250/227; 356/416; 356/446
[58] Field of Search ................... 356/402, 405–407, 356/416, 445–448; 250/227, 226

[56] References Cited

U.S. PATENT DOCUMENTS

| | | | |
|---|---|---|---|
| 3,463,595 | 8/1969 | Blanc et al. | 356/201 |
| 3,473,878 | 10/1969 | Schweitzer | 356/446 |
| 3,500,054 | 3/1970 | Lasalle et al. | 250/227 |
| 3,707,030 | 12/1972 | Hunter et al. | 356/416 |
| 3,806,256 | 4/1974 | Ishak | 356/446 |
| 4,076,421 | 2/1978 | Kishner | 356/446 |
| 4,240,751 | 12/1980 | Linnecke et al. | 356/409 |

*Primary Examiner*—F. L. Evans
*Attorney, Agent, or Firm*—Lane, Aitken & Kananen

[57] ABSTRACT

In a colorimetry system, the test surface, the color of which is to be measured, is illuminated by a fiber optic cable. Light transmitting ends of the optic fibers of the fiber optic cable are uniformly distributed into an annulus with the transmitting ends of the optic fibers pointed inwardly at 45 degrees toward the axis of the annulus. A light pipe, or a second fiber optic cable, is positioned to have one end on the axis of the annulus to receive diffusely reflected light from the test surface and transmit the reflected light to photodetectors through different color filters. The output signals of the photodetectors are applied to the colorimetry console which converts the photodetector signals to standard color index values.

11 Claims, 6 Drawing Figures

4,464,054

COLORIMETER INSTRUMENT WITH FIBER OPTIC RING ILLUMINATOR

BACKGROUND OF THE INVENTION

This invention relates to colorimetry systems and, more particularly, to a colorimetry system with a ring of optic fibers arranged to illuminate the test surface on which the colorimetry measurements are to be made.

In colorimetry, it is conventional to illuminate the test surface to be measured and direct the light diffusely reflected from the test surface to photodetectors through different color filters. The electrical output signals of the photodetectors provide a quantitative measurement of the color of the test surface. The Gardner/Neotec Division of Pacific Scientific Company presently manufactures and markets colorimetry instruments in which light is transmitted to the sample from a light source and the light diffusely reflected from the sample is transmitted to three photodetectors with a different color filter placed in the light path to each photodetector. The output signals of the photodetectors are transmitted to the Gardner/Neotec XL-800 Series colorimeter console in which the signals from the photodetectors are converted to digital values and mathematic operations are performed on the digital values by a microprocessor for calibration and conversion into standard color index values.

The above described instruments give accurate quantitative color measurements as the eye perceives color. However, when the measurements are made on a textured surface, there may be some variation in the color measurement, depending upon the angular orientation of the test surface being measured. One of the objects of the present invention is to provide a colorimetry instrument in which the color measurements will not vary with the angle of the test surface even when the test surface is highly textured.

SUMMARY OF THE INVENTION

In accordance with the present invention, a fiber optic cable is provided to transmit the light from a light source to the test surface. The fibers of the fiber optic cable are arranged into a ring at the transmitting end and are arranged to direct the light transmitted by the individual fibers inwardly toward the axis of the ring. The system defines a measurement plane, for receiving a test surface on which the color measurements are to be made, positioned perpendicularly to the axis of the ring so that each of the fibers is pointed at the measurement plane at the same angle. With this arrangement, a test surface at the measurement plane will be illuminated from an annulus of the fiber ends surrounding the test surface area and the light reflected generally perpendicularly from the surface will be diffusely reflected light. Means are provided to receive this diffusely reflected light and transmit it to three photodetectors through different color filters. The output signals from the photodetectors are transmitted to the colorimeter console where the signals are calibrated and converted to standard color index values.

In the first embodiment of the invention, the light source and fiber optics are mounted in a housing having an upper, horizontal wall to define the measurement plane to receive a downwardly facing test surface on which the color measurements are to be made. The fiber optic ring is positioned adjacent to this upper, horizontal surface to illuminate the downward facing test surface through an aperture in the upper housing wall. A light pipe is positioned on the axis of the fiber optic ring to receive light diffusely reflected from the surface. The light pipe transmits the light to three photodetectors, the output signals of which are transmitted to the colorimeter console for calibration and conversion to standard color index values.

In accordance with a second embodiment of the invention, instead of using a light pipe, a fiber optic cable is used to transmit the light diffusely reflected from the test surface to the photodetectors. In this embodiment, a sensing head is connected to the photodetectors and the light source through a flexible cable containing both the fiber optics used to illuminate the measurement plane and to transmit the light from the measurement plane back to the photodetectors. This arrangement facilitates the measurement of the color of surfaces on large or cumbersome objects which cannot be conveniently positioned on the housing containing the photodetectors and light source.

By illuminating the surface with a fiber optic ring arranged to direct the light inwardly at the measurement plane from all angles of rotation about an axis perpendicular to the measurement plane, a color measurement is achieved which has no variation with rotation of the test surface with respect to the illuminating system even when the surface is highly textured. This advantage is achieved in a system in which the color is measured as the eye perceives the color.

DESCRIPTION OF THE PREFERRED EMBODIMENTS

Figure 1:
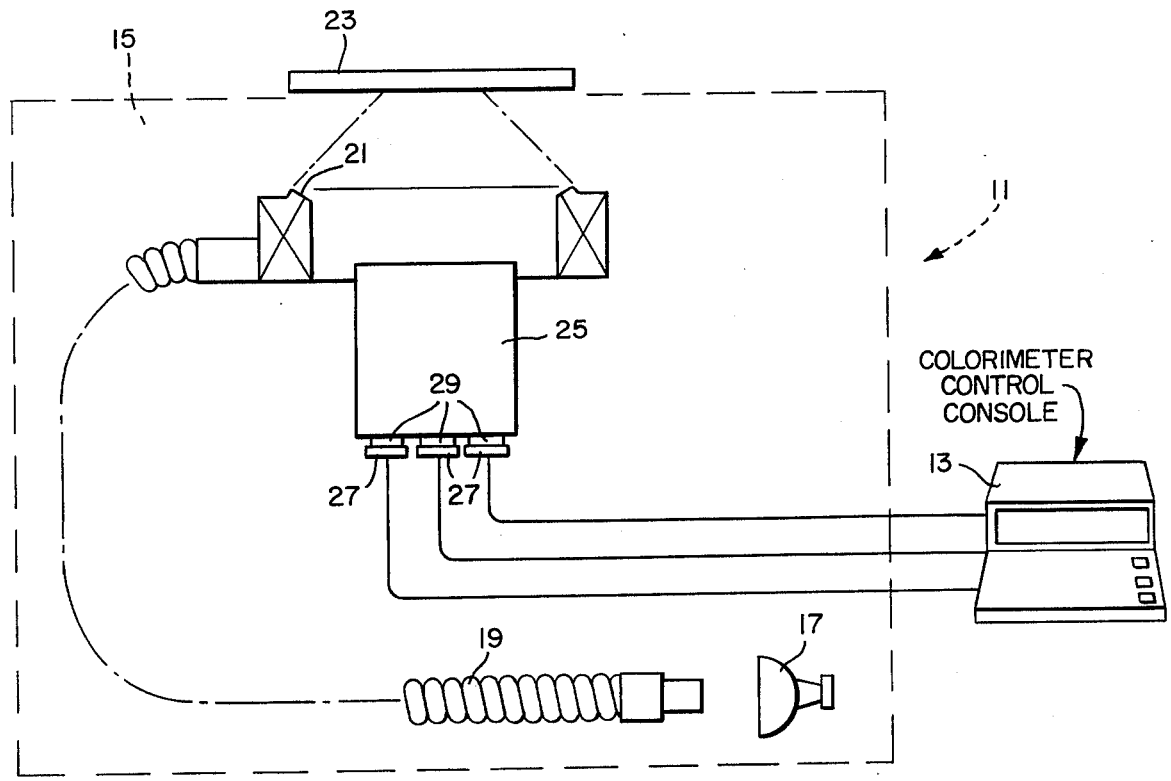
FIG. 1 is a schematic diagram of one embodiment of the invention.

As shown in FIG. 1, the colorimetry system of the present invention comprises a color sensor 11, which is electrically connected to a colorimeter console 13. The colorimeter console 13 is available on the market from the Gardner/Neotec Division of Pacific Scientific Company and is identified as the XL-800 Series colorimeter control console. The colorimeter console is designed to receive analog signals from the photodetectors of a color sensor which detects diffusely reflected light from a test surface through different color filters. The control console converts the analog signals to digital values and then performs mathematical operations on the digital values by means of a microprocessor to calibrate the received signals and convert the received signals to standard color index values in order to provide a quantitative measurement of the color of the test surface. The calibration is carried out by first taking a color reading by the color sensor from a standard tile and using the values obtained from the standard tile to calibrate the values read from a test surface, the color of which is being measured. Prior to the present invention, the XL-800 Series control console from Gardner/Neotec was used with the Gardner/Neotec XL-805 sensor and the Gardner/Neotec XL-825 color sensor and it is used in the same manner with the color sensor 11 of the present invention.

The color sensor 11 of the present invention, as shown in FIG. 1, comprises a housing 15 in which there is mounted a light source 17 arranged to direct a beam of light into one end of a fiber optic cable 19. The other end of the fiber optic cable 19 has the ends of fibers of the cable arranged in a ring or annulus 21 with the fibers arranged to point toward the axis of the annulus upwardly at an angle of 45 degrees to the axis of the annulus. The upper wall of the housing 15 defines a horizontal measuring plane at which the test sample surface (or standard tile for calibration) is to be positioned for a color measurement. In FIG. 1, an exemplary test sample is designated by the reference number 23. Each optic fiber will transmit a beam of light which spreads as it leaves the fiber and the axis of the beam from each fiber will be at 45 degrees to the measurement plane. The annulus of fiber ends 21 transmits the light to the lower surface of the sample 23, on which lower surface the color measurement is to be made. As a result of the illumination of light from the annulus 21 of fiber ends, light will be diffusely reflected from the sample 23 to a light pipe 25, which is a cylinder of transparent or light transmitting material and which transmits the light reflected from the surface 23 to three photodetectors 27. Each end of the light pipe 25 is provided with a light diffuser. The axis of the light pipe 25 coincides with the axis of the annulus 21 of the transmitting ends of the optic fibers. The photodetectors 27 are inside the extension of the cylinder defined by the cylindrical surface of the light pipe 25. Different color filters, or, in other words, filters with different light wavelength transmitting bandwidths 29, are positioned between the photodetectors 27 and the light pipe 25. The output signals generated by the photodetectors 27 are applied to the colorimeter console 13.

Figure 2:
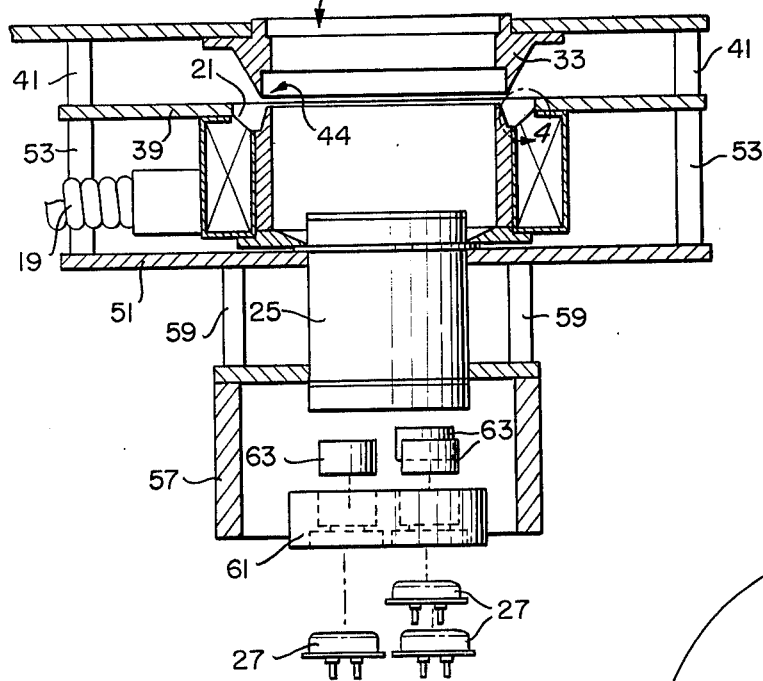
FIG. 2 is a partial sectional, partially exploded view in elevation showing the relationship of the ring of illuminating fibers to the light pipe for transmitting the light reflected from the test surface to the photodetectors.
Figure 4:
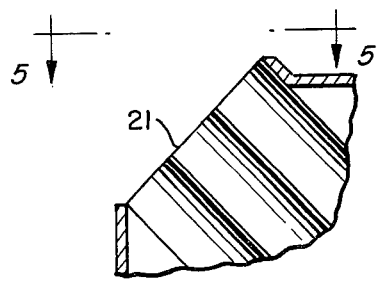
FIG. 4 is an enlarged sectional view within the circle 4 of FIG. 2 illustrating the orientation of the optic fibers at the transmitting ends where they are formed into an annulus.
Figure 5:
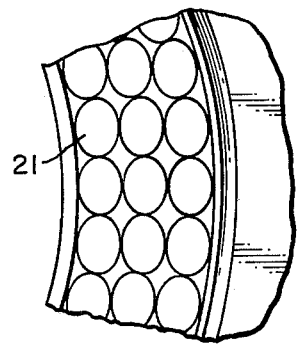
FIG. 5 is an enlarged view of the end of the optic fibers at the annulus taken along the line 5—5 of FIG. 4.

As shown in FIG. 2, the housing of the color sensor 11 has a top wall 31, which has mounted therein an aperture ring 33 defining an aperture 35 through the top wall 31. The surface on which the color measurements are to be made is placed over the aperture 33 facing downward. The optic fibers from the cable 19 are distributed in an annular or doughnut-shaped housing 37 so that their ends are evenly distributed in the form of a ring or annulus 21, and, as best shown in FIGS. 4 and 5, the ends of the optic fibers are arranged to point at 45 degrees with respect to the sample surface placed over the aperture 33, or, in other words, at 45 degrees to the axis of the ring or annulus defined by the ends of the optic fibers. The individual fiber ends preferably are contiguous around the annulus and are two to three fibers deep across the width of the annulus. The annular housing 37 is positined against a plate 39 defining a circular aperture and the annulus 21 defined by the transmitting ends of the optic fibers fits just inside the perimeter of this circular aperture. The plate 39 is separated from the upper wall 31 of the sensor housing by spacer bars 41. The spacer bars 41 and the plate 38 determine the vertical position of the annulus 21 of fiber ends relative to the measurement plane. The annular housing 37 fits around a cylindrical aperture ring 43. The aperture ring 43 is positioned so that there is an annular gap 44 defined between the aperture ring 35 and the aperture ring 43 and the light is transmitted from the annulus 21 of optical fibers to the aperture 35 through the gap 44. Positoned against the lower end of the aperture ring 43 is an alignment ring 49. The alignment ring has a shoulder defined in the upper, outer edge thereof to receive the fiber optic housing 37 and defines an inner aperture to engage the cylindrical wall of the light pipe 25 to thereby fix the alignment of the annulus 21 of the ends of the optic fibers with the light pipe 25. The light pipe 25 is positioned in a circular aperture in a mounting plate 51 which is separated from the plate 39 by spacers 53.

Figure 3:
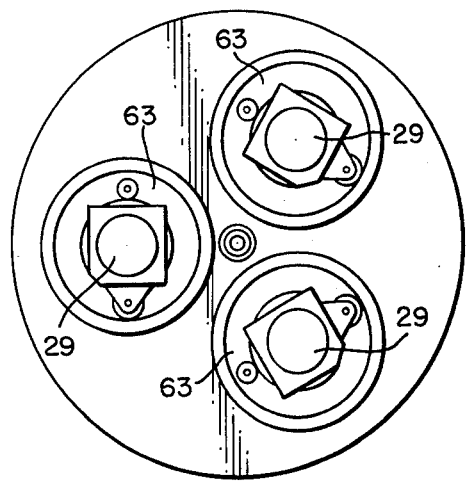
FIG. 3 is a top plan view of the filter holder of the system shown in FIG. 2 showing the positioning of the color filters of the color sensor.

The lower end of the light pipe 25 extends through a cover plate 55 of a detector chamber 57. The cover plate and, therefore, the detector chamber 57, is positioned with respect to the plate 51 by means of spacers 59. Mounted within the detector chamber 57 is a filter holder 61 in which are mounted filter assemblies 63 and the photodetectors 27. In FIG. 2, the filter holder, filter assemblies and photodetectors are shown in an exploded view. The filter assemblies 63 which are mounted in recesses defined in the top of the filter holder 61 and, as shown in FIG. 3, each contains one of the color filters 29. The photodetectors 27 are mounted in recesses defined in the bottom of the filter holder 61 and a light communication path is defined between the filter assembly recesses and the photodetectors 27 so that the light transmitted through the fitlers 29 inpinges upon the photodetectors 27. The recesses containing the filter assemblies 63 are located to position the filters 29 so that they are inside the extension of the cylinder defined by the outer cylindrical wall of the light pipe 25 to receive the light transmitted through the light pipe reflected from the test surface.

With the above described arrangement, a test surface placed over the aperture 35 will be illuminated from all angles of rotation about an axis perpendicular to the surface 35 and the resulting diffusely reflected light will be transmitted by the light pipe 25 through the filters 29 to the photodetectors 27. The resulting signals produced by the photodetectors 27 will be transmitted to the colorimeter console 13 for calibration and conversion to standard color index values. Because the surface is illuminated from what is in effect a ring source of light defined by the annulus 21 of fiber optic ends, the resulting color measurement will not vary with the angular position of the test surface placed over the aperture 35 and, thus, the system of the present invention provides an ideal system for measuring the color of textured surfaces.

Figure 6:
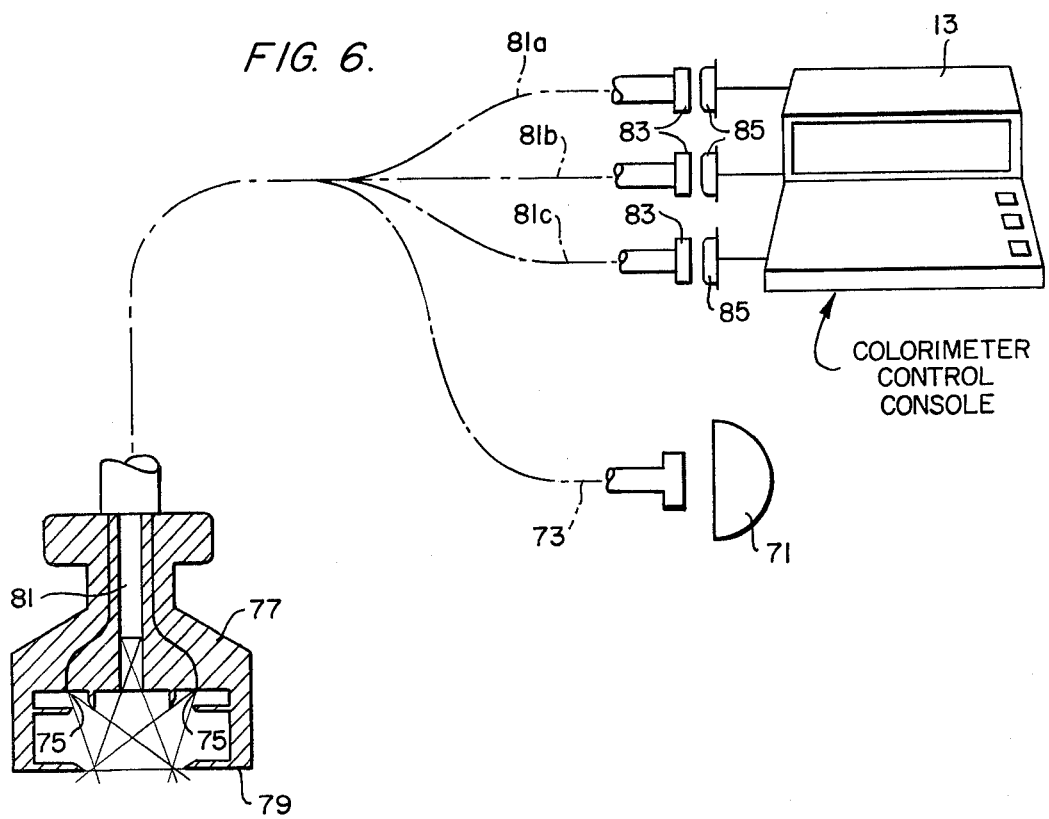
FIG. 6 is a schematic diagram of an alternative embodiment of the invention.

In the second embodiment of the invention schematically illustrated in FIG. 6, light from a source 71 is transmitted into the receiving end of a fiber optic cable 73. The other end of the fiber optic cable 73 is formed into a annulus 75, like the annulus 21 in the embodiment of FIG. 1. The annulus 75 is formed in a color sensing head 77. The sensing head 77 has a planar surface 79 to define a measurement plane at which the test surface is to be positioned. As in the embodiment of FIG. 1, the optic fibers forming the annulus 75 are pointed at the axis of the annulus at an angle of 45 degrees and are pointed toward the measurement plane defined by the planar surface 79. Diffusely reflected light from the measurement plane is received by another fiber optic cable 81. The end 82 of the fiber optic cable 81 receiving the diffusely reflected light is positioned on the axis of the annulus 75 of optic fibers perpendicularly to the measurement plane. The fiber optic cable 81 forms a common flexible cable with the fiber optic cable 73 and, at its other end opposite from the receiving end 82, the cable 81 is divided into three parts 81a, 81b and 81c. Light transmitted through the three parts of the fiber optic cable 81a, 81b and 81c are transmitted through color filters 83 to photodetectors 85 and the resulting signals generated by the photodetectors 85 are applied to the colorimeter console 13 identical to the control console 13 employed in the system of FIG. 1. With this arrangement, the sensing head 71 is optically connected through a combined flexible optic cable, comprising the fiber optic cable 73 and the fiber optic cable 81, to the light source 71 and to photodetectors 85 so as to receive light from the source 71 and transmit it to the test surface and to receive the diffusely reflected light from the test surface and transmit it to the photodetectors 85. Because the sensing head is on the end of a flexible cable, the system of FIG. 6 advantageously can measure surfaces of cumbersome objects which could not be conveniently placed on the housing of the color sensor of the system of FIG. 1. Because the illumination of the surfaces is by means of a fiber optic ring, the color measurement made by the system of FIG. 6 is not sensitive to the angular position of the test surface with respect to the sensing head 77 and, thus, the system of FIG. 6, like that of FIG. 1, is particularly advantageous in measuring the color of textured surfaces.

The above description is of preferred embodiments of the invention and modification may be made thereto without departing from the spirit and scope of the invention, which is defined in the appended claims.

What is claimed is:

1. A color sensing system comprising means defining a measurement plane adapted to receive at said measurement plane a test surface for purposes of making a color measurement, a source of light, a fiber optic cable having one end positioned to receive a beam of light directly from said source and the other end positioned to transimit light to said measurement plane, the ends of the optic fibers in said other end of said fiber optic cable being formed into and uniformly distributed in an annulus with the ends of said fibers pointed toward said test surface plane and inclined toward the axis of said annulus, at least one photodetector, and means to receive light diffusely reflected from said measurement plane and transmit the light to said photodetector.

2. A color sensing system as recited in claim 1, wherein a color filter is located in the path of the light transmitted to said photodetector.

3. A color sensing system as recited in claim 1, comprising at least three photodetectors and a different color filter in the path of the light transmitted to each photodetector.

4. A color sensing system as recited in claim 1, wherein the ends of the fibers in said annulus are contiguous.

5. The color sensing system as recited in claim 4, wherein the face of said annulus defined by the ends of said fibers is a plurality of fibers wide.

6. The color sensing system as recited in claim 1, wherein said means to transmit light reflected from said measurement plane has light receiving means positioned on the axis of said annulus to receive light reflected perpendicularly from said measurement plane.

7. The color sensing system as recited in claim 6, wherein said light transmitting means comprises a light pipe and wherein a plurality of photodetectors are positioned to receive light transmitted through said light pipe.

8. The color sensing system as recited in claim 6, wherein said means to transmit light reflected from said surface to said photodetector comprises a fiber optic cable.

9. The color sensing system as recited in claim 1, wherein the ends of said optic fibers formed in said annulus are pointed at an angle of 45 degrees with respect to said measurement plane.

10. The color sensing system as recited in claim 1, wherein the ends of said fibers defining said annulus are pointed toward the axis of said annulus at an equal angle with respect to said axis.

11. A color sensing system comprising means defining a measurement plane adapted to receive at said measurement plane a test surface for purposes of making a color measurement, a source of light, a fiber optic cable having one end positioned to receive light from said source and the other end positioned to transmit light to said measurement plane, the ends of the optic fibers in said other end of said fiber optic cable being formed into and uniformly distributed in an annulus, a cylindrical light pipe positioned on the axis of said annulus to receive light reflected perpendicularly from said measurement plane, and a plurality of photodetectors within the extension of the cylinder defined by the cylindrical outer surface of said light pipe positioned to receive light reflected from said measurement plane and transmitted through said light pipe.

* * * * *